US00PP30569P2

(12) United States Plant Patent
Korlipara

(10) Patent No.: US PP30,569 P2
(45) Date of Patent: Jun. 11, 2019

(54) ***PENSTEMON* PLANT NAMED 'TNPENDB'**

(50) Latin Name: ***Penstemon* hybrid**
Varietal Denomination: TNPENDB

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/932,828

(22) Filed: Apr. 30, 2018

(51) Int. Cl.
*A01H 5/02* (2018.01)
*A01H 6/68* (2018.01)

(52) U.S. Cl.
USPC ..... Plt./465
CPC ..... *A01H 6/68* (2018.05); *A01H 5/02* (2013.01)

(58) Field of Classification Search
USPC ..... Plt./465
CPC ..... A01H 5/02
See application file for complete search history.

(56) References Cited

PUBLICATIONS https://www.growertalks.com/Newsletters/View/?article=2462; Feb. 22, 2018; 11 pages.*

* cited by examiner

*Primary Examiner* — Kent L Bell
(74) *Attorney, Agent, or Firm* — Klarquist Sparkman, LLP

(57) ABSTRACT

A new and distinct cultivar of *Penstemon* plant characterized by glossy, dark purple leaves, lavender to violet flowers, short, compact, upright, well branched habit, attractive deep purple seed heads, and excellent vigor.

2 Drawing Sheets

Botanical denomination: *Penstemon* hybrid.
Variety designation: 'TNPENDB'.
Trademark designation: Dakota™ Burgundy
Cross Reference to: *Penstemon digitalis* 'TNPENDV', U.S. Plant patent application Ser. No. 15/932,827

BACKGROUND OF THE INVENTION

The present invention relates to a new and distinct cultivar of *Penstemon*, given the name, 'TNPENDB'. *Penstemon* is in the family Plantaginaceae (formerly Scrophulariaceae). This plant originated in a controlled breeding plan to create a compact series with good flowering. The parents are unknown, unnamed proprietary plants. This cultivar was selected for its dark purple foliage, short habit, lavender to violet flowers, hardiness, and vigor. It is an ideal plant for a sunny border in full sun.

Compared to plants of *Penstemon digitalis*, an unpatented plant, the new cultivar is shorter and more compact, flowers are more lavender to violet rather than white and foliage color that is tinted purple with winter temperatures rather than green.

Compared to plants of *Penstemon* 'Mystica', an unpatented seed strain, the new cultivar is shorter and more compact, flowers are more lavender to violet than white.

Compared to *Penstemon* 'Dark Towers', U.S. Plant Pat. No. 20,013, the new cultivar has a shorter and more compact habit, flowers are more lavender to violet rather than pink.

Compared to *Penstemon* 'TNPENDV', U.S. Plant patent application Ser. No. 15/932,827, the new cultivar has dark purple leaves instead of green leaves.

*Penstemon* 'TNPENDB' is uniquely distinguished by its:
1. glossy, dark purple leaves,
2. lavender to violet flowers,
3. short, compact, upright, well branched habit
4. attractive deep purple seed heads, and
5. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
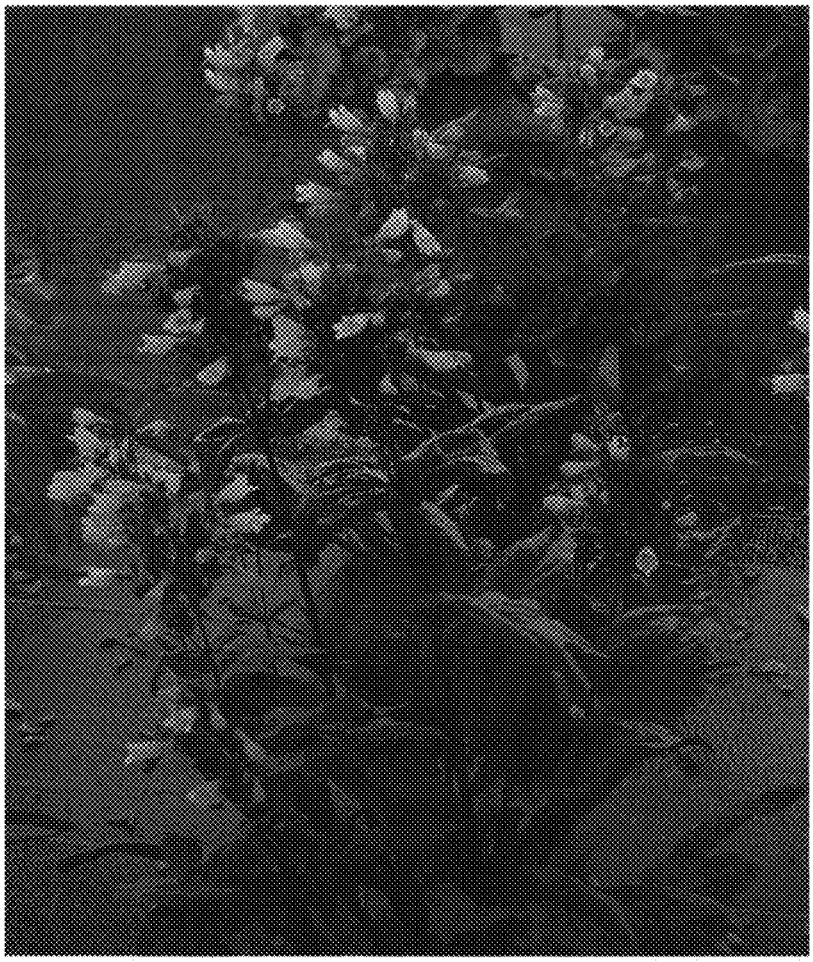
FIG. 1 shows the habit of an eight-month-old plant in the trial field in August in Canby, Oreg.
Figure 2:
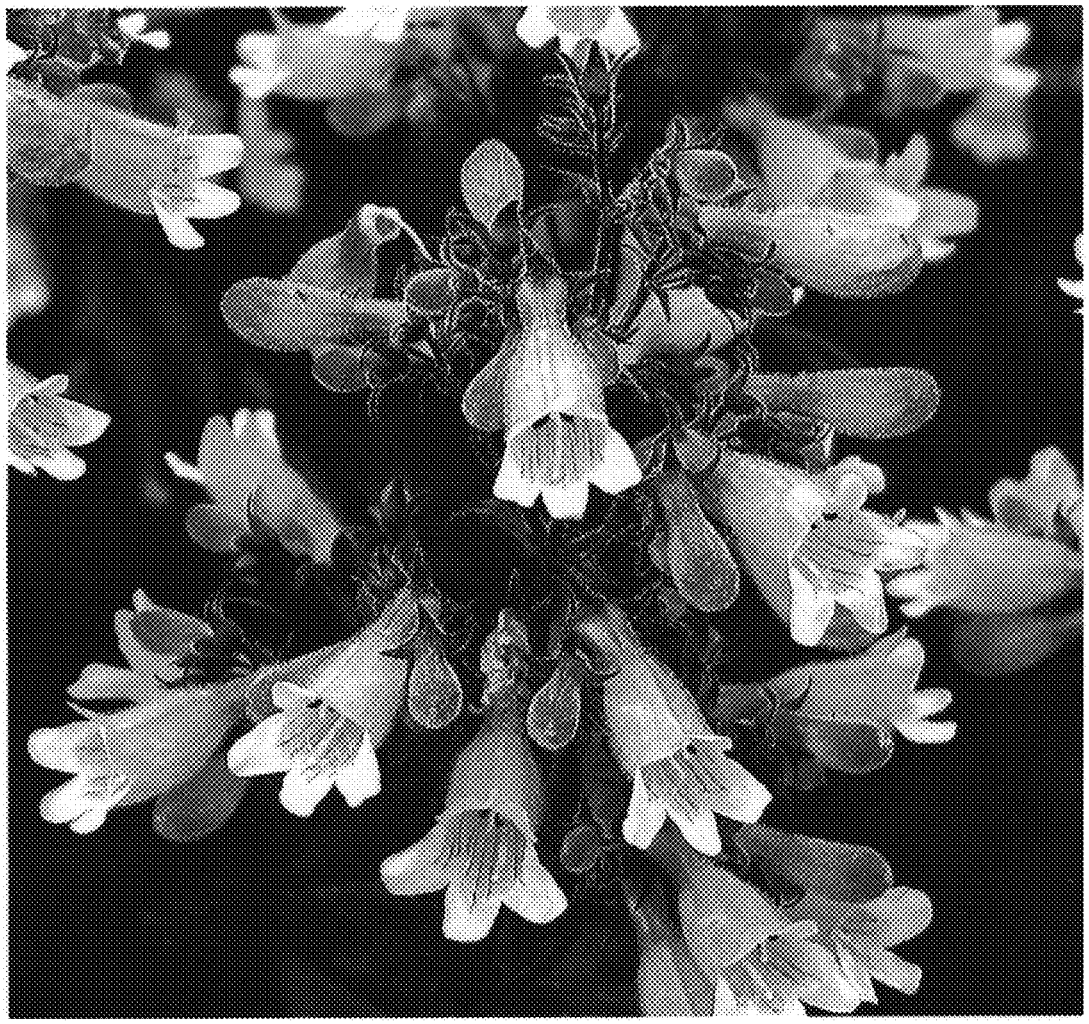
FIG. 2 is a close-up of flowers showing tube Purple Violet N81A with bee tracks Purple Violet N81A.

The following is a detailed description of the new *Penstemon* cultivar based on observations of nine-month-old specimens grown outside in the trial field in full sun in Canby, Oreg. in October. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* 5th edition, 2007.

Plant:

*Type*.—Herbaceous perennial.

*Form*.—Upright, basal clump, up to 7 leafy flowering stems from base.

*Size*.—Grows to 45 cm wide and 55 cm high to top of inflorescence.

*Crown count*.—13.

*Roots*.—Fibrous, with many downward growing and a few laterals, ivory in color, Yellow White 158D, roots develop easily from cuttings from the crown.

*Vigor*.—Excellent.

*Cold hardiness*.—USDA Zone 3-8.

Leaf (basal):

*Type*.—Simple.

*Arrangement*.—Rosette.

*Shape*.—Lanceolate.

*Venation*.—Pinnate.

*Margins*.—Serrulate.

*Apex*.—Acute.

*Base*.—Attenuate.

*Blade size*.—Grows to 23 cm long and 4.1 cm wide.

*Surface texture*.—Both sides glabrous.

*Petiole*.—Petiole clasping to 9.5 cm long and 4 mm wide, Greyed Purple 187A.

*Leaf color*.—Topside Yellow Green 147A at base blending to Greyed Purple N186A with veins Greyed Purple N186C, bottom side Green 137B at base blending to Greyed Purple N186A blotched with Green 137B, veins Greyed Purple N186C.

Leaf (stem):

*Type*.—Simple.

*Habit*.—Upright.

*Arrangement*.—Opposite.

*Shape*.—Lanceolate.

*Venation*.—Pinnate, main vein on top Greyed Purple N186C, bottom side Greyed Purple N186C.

*Margins*.—Serrate.

*Apex*.—Acute.

*Base*.—Attenuate.

*Blade size*.—Grows to 10.4 cm long and 3.3 cm wide.

*Surface texture*.—Glabrous on both sides.

*Petiole*.—None, sessile.

*Leaf color*.—Topside Greyed Purple N186A, bottom side between Greyed Purple N187A and Greyed Purple 187A.

*Stem*.—Upright, up to 31 cm long and to 6mm (at the base), glabrous at base to glandular pubescent toward rachis, internodes grow to 9.5 cm long, Greyed Purple 187A.

Inflorescence:

*Type*.—Terminal, many flowered, loose thyrse.

*Number of flowers per inflorescence*.—50 to 100.

*Rachis size*.—Grows to 12 cm long and 10 mm wide, sparsely pubescent, Greyed Purple 187A.

*Peduncle*.—Grows to 6 cm long and 2.5 mm wide, pubescent, Greyed Purple 187A.

*Pedicels*.—Grows to 5 mm long and 1 mm wide, pubescent, Greyed Purple 187A.

*Bloom period*.—June to frost in Canby, Oreg.

Flower bud:

*Size*.—1.9 cm long and to 5 mm wide.

*Description*.—Closed tubular.

*Color*.—Topside Greyed Purple 187C, bottom side White 155C.

Flower:

*Type*.—Zygomorphic, perfect.

*Shape*.—Tubular, bilabiate.

*Size*.—Grows to 3.3 cm long and 1.5 cm wide.

*Corolla description*.—Grows to 3 cm long and 1.5 cm wide; tube is bulbous in the calyx for 5 mm long and 4 mm wide, narrowing then widening for 2.3 cm and flaring to 1.5 cm wide, 5 lobes, the two smaller top lobes flare back (each 5 mm wide and to 6 mm deep) and two larger lateral lobes curl back slightly (10 mm wide and 10 mm deep), and the lower lobe flares curls back slightly (7 mm wide and 6 mm deep), lobe margins entire, tips acute; outside glandular pubescent, inside sparsely pubescent; outside color bulbous section Purple Violet N81B on top, Violet 85D bottom, inside color lobes and bulbous section Purple Violet N81C, tube Purple Violet N81A with bee tracks Purple Violet N81A.

*Calyx description*.—5 mm deep and 5 mm wide, 5 lobes, each lobe ovate in shape, 4 mm long and 4 mm wide, margins entire, tip acuminate, base cuneate, both sides between Greyed Purple N187A and Greyed Purple 187A, both sides pubescent.

*Pistil description*.—1, 2.7 cm long, ovary 7 mm long and 2 mm wide, Greyed Purple 187B; style 2 cm long and less than 1 mm wide, style Greyed Orange N170 D, stigma White NN155C.

*Stamen description*.—5, one sterile without an anther, held within the corolla, filament 20 mm long and Purple Violet N81C, fertile anthers 2 mm long, Brown N200B, filaments 22 mm long, Purple Violet N81C.

*Pollen*.—Scarce to moderate, White NN155C.

*Fragrance*.—None.

*Lastingness*.—A flower lasts 5 to 6 days.

Fruit:

*Type*.—Capsule.

*Fertility*.—Fair.

*Size*.—10 mm deep and 6 mm wide.

*Shape*.—Conical.

*Color*.—Greyed Purple 187A.

Seed:

*Shape*.—Irregular.

*Size*.—2 mm long.

*Color*.—Black 202A.

Pests and diseases: The new cultivar is typical to the genus. No problems have been found in Canby, Oreg.

I claim:

1. A new and distinct cultivar of *Penstemon* plant substantially as illustrated and described herein.

* * * * *